United States Patent [19]

Woo

[11] 4,088,680

[45] May 9, 1978

[54] LINEAR ALKYL HYDROCARBYLOXYBENZENE DISULFONATES

[75] Inventor: Gar Lok Woo, Tiburon, Calif.

[73] Assignee: Chevron Research Company, San Francisco, Calif.

[21] Appl. No.: 733,588

[22] Filed: Oct. 18, 1976

Related U.S. Application Data

[60] Continuation of Ser. No. 546,665, Feb. 3, 1975, abandoned, which is a continuation-in-part of Ser. No. 256,504, May 24, 1972, abandoned, which is a division of Ser. No. 66,088, Aug. 21, 1970, Pat. No. 3,707,352.

[51] Int. Cl.² .................. C07C 143/42; B08B 3/00
[52] U.S. Cl. .................. 260/512 R; 252/121; 252/558; 8/137
[58] Field of Search .................. 260/512 R, 501.19

[56] References Cited

U.S. PATENT DOCUMENTS

| | | | |
|---|---|---|---|
| 2,178,830 | 11/1939 | Bruson | 260/512 R |
| 2,271,635 | 2/1942 | Flett | 260/512 R |
| 2,828,334 | 3/1958 | Groote | 260/512 R |
| 3,766,254 | 10/1973 | Sharman et al. | 260/512 R |

Primary Examiner—Nicky Chan
Attorney, Agent, or Firm—D. A. Newell; John Stoner, Jr.

[57] ABSTRACT

Detergent active materials capable of heavy duty washing in the absence of phosphates comprising linear alkyl hydrocarbyloxybenzene disulfonates of the formula

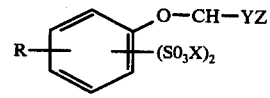

in which R is linear alkyl of 10 to 24 carbon atoms, X is H or a water-soluble salt-forming cation, Z is H, or an alkyl group of 1 to 6 carbon atoms and Y is H, alkyl of 1 to 6 carbon atoms, alkenyl of 2 to 6 carbon atoms, or aralkyl of 7 to 9 carbon atoms, Y and Z may be polymethylene chain of 2 to 7 carbon atoms, the sum of the aliphatic carbon atoms in R and —CH—YZ is from 17 to 25, and for this purpose an aromatic carbon atom is considered equal to ⅔ aliphatic carbon atom.

2 Claims, No Drawings

LINEAR ALKYL HYDROCARBYLOXYBENZENE DISULFONATES

CROSS-REFERENCE TO RELATED APPLICATIONS

This application is a continuation of application Ser. No. 546,655, filed Feb. 3, 1975, and now abandoned which, in turn, is a continuation-in-part of U.S. application Ser. No. 256,504, filed May 24, 1972, and now abandoned, which, in turn, is a division of U.S. application Ser. No. 66,088, filed Aug. 21, 1970, now U.S. Pat. No. 3,707,352.

BACKGROUND OF THE INVENTION

This invention is concerned with linear alkyl hydrocarbyloxybenzene disulfonates which are effective in detergent applications as detergent actives.

Increased concern over water pollution has produced significant changes in household detergents. Initially, major emphasis has been placed on producing biodegradable surface-active components for detergents. The shift to linear surface-active materials, including linear alkylbenzene sulfonate (LAS) and alpha-olefin sulfonates, etc., has reduced pollution attributed to nonbiodegradability.

However, the above-mentioned surface-active materials are inadequate in terms of soil removal in the absence of phosphate builders. Increasing evidence appears to indicate that phosphates contribute to the growth of algae in the nation's streams and lakes. This algae growth poses a serious pollution threat to the maintenance of clear, good domestic water supplies.

Consequently, there has developed a need for detergent active materials which will function successfully in the absence of phosphate builders. Recently, certain non-phosphate building materials have been proposed as replacements for the phosphates. Thus, materials such as the polysodium salts of nitrilotriacetic acid, ethylene diamine tetraacetic acid, copolymers of ethylene and maleic acid, and similar polycarboxylic materials have been proposed as builders. These materials, however, when employed with conventional detergent actives such as LAS, have, for one reason or another, not proved to be quite as effective as phosphates in detergent formulations. For example, some of the materials have proven to be insufficiently biodegradable to meet present and anticipated requirements.

It is therefore desirable to provide compounds which are effective as detergent active materials in the absence of phosphate builders and are also sufficiently biodegradable that their use results in contributing neither foam producers nor phosphates to the water supply.

In addition, in the past, with heavy duty detergents, it has been thought that to achieve good soil removal it was necessary to maintain a high pH in washing solutions. This concept, which began with the strongly alkaline laundry soaps, has continued to the present day LAS-phosphate combinations which are in widespread use in heavy duty detergent formulations. One apparent reason for this is that the alkylbenzene solfonate detergents are not effective in heavy duty detergent formulations in the absence of a builder. The phosphate builders, for example, must be employed at a pH greater than 9 to be effective, and even the newer builders such as sodium nitriloacetate have a pH of about 9 in solution. The advantages to be gained with heavy duty detergents which may be employed at neutral pH are many. Deleterious effects from skin contact are lessened. Enzyme-type soil looseners may be more easily combined in neutral solutions. Injury to fabrics is minimized. It is, therefore, desirable to provide detergent active materials which, in addition to the previously mentioned non-polluting characteristics, achieve their maximum detergency at or near neutral pH.

The formulation of liquid heavy duty detergent compositions achieves many desirable results. They are easy to package and measure, and their use opens the possibility of automatic dispensing in washing machines. However, in the past it has been impracticable to formulate heavy duty detergents in liquid form because of the insufficient solubility of the inorganic ingredients (phosphate builders, etc.) required for heavy duty applications and the high cost of organic substitutes for such inorganic ingredients. It is therefore highly desirable to provide detergent active materials having good water solubility and which, because of their excellent detergency without builders, can be formulated into effective, reasonably priced heavy duty liquid detergent formulations.

SUMMARY OF THE INVENTION

It has now been found that effective heavy duty detergent compositions may be formulated without the necessity of phosphate builders by employing as the detergent active materials linear alkyl hydrocarbyloxybenzene disulfonates of the formula

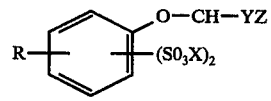

in which R is linear alkyl of 10 to 24 carbon atoms, X is H or a water-soluble salt-forming cation, Z is H, an alkyl of 1 to 6 carbon atoms and Y is H, alkyl of 1 to 6 carbon atoms, alkenyl of 2 to 6 carbon atoms, phenyl or alkaryl of 7 to 9 carbon atoms, Y and Z may be a polymethylene chain of 2 to 7 carbon atoms, the sum of the aliphatic carbon atoms in R and Y and Z is from 17 to 25, and for this purpose an aromatic carbon atom is considered equal to 2/3 aliphatic carbon atom.

The compounds of this invention do not require the presence of a builder to achieve good detergency, and are effective over a broad pH range (from 6 to 10 or even higher). THus, washing at a pH of 6.5 to 8.0, preferably 6.5 to 7.5, will give effective soil removal while securing the previously mentioned advantages which inhere in the use of neutral washing solutions. Further, the compounds may be easily compounded into effective liquid heavy duty formulations because of the substantial solubility of the compounds in water and because of the lack of need for adjunctive inorganic additives such as builders.

DESCRIPTION OF PREFERRED EMBODIMENTS

The salt-forming cation X may be any of numerous materials such as alkali metal, alkaline earth metal, ammonium, or various organic cations. Examples of suitable organic cations include amino materials, particularly those derived from lower alkanolamines, i.e. those of 1 to 6 carbon atoms.

Illustrative cations are those of the following structures: $NH_2^+(CH_2CH_2OH)_2$ or $HN^+(CH_2CH_2OH)_3$ The alkali metal cations are preferred, and sodium ions are particularly preferred.

The alkyl groups represented by R are, as previously noted, linear, although the presence of a random methyl radical upon the linear chain, for example, may not adversely affect the performance of the compound. By linear it is meant that the alkyl group itself is straight chain; the point of attachment is not significant. Alkyl radicals representative of R include hexadecyl, heptadecyl, octadecyl, nonadecyl, eicosyl, heneicosyl, docosyl, tricosyl and tetracosyl. Heptadecyl, octadecyl, nonadecyl, eicosyl, and heneicosyl groups are preferred.

R may be attached to the benzene nucleus at any position relative to —O—CH—YZ. In most instances, since the production of ortho and para alkylphenols is most easily effected by the usual phenol alkylation methods, the position of R will be ortho or para to —O—CH—YZ. As noted, the attachment of the benzene ring to R may be at any point on the alkyl chain. The preferred compounds will thus have the formula

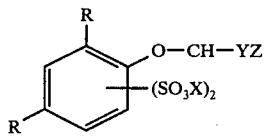

in which one R is linear alkyl of 10 to 24 carbon atoms and the other is H and Y and Z are as indicated.

The hydrocarbyl groups represented by —CH—YZ include saturated and unsaturated aliphatic groups such as methyl, ethyl, propyl, butyl, pentyl and hexyl groups, corresponding unsaturated groups including allyl, methyl allyl, ethyl allyl, 2-propenyl, 2- and 3-butenyl, 2-, 3- and 4-pentenyl, and branched materials such as isopropyl, 2-methyl propyl, etc. Cyclic saturated and unsaturated groups can be employed such as cyclohexyl, benzyl (phenylmethyl), tolylmethyl, etc. Preferably Y and Z are H or alkyl groups of 1 to 6 carbon atoms. In the preferred compounds —CH—YZ is methyl or ethyl.

The compounds of this invention are produced by alkylation of phenol with a suitable alkylating agent followed by sulfonation of the alkylphenol product with a suitable sulfonating agent to produce a material having a major portion of materials containing two disulfonic acid groups. The alkylphenol disulfonic acid product is then neutralized with sufficient base to convert the phenolic hydroxyl to a metal phenolate. This material is then reacted with an alkylating agent such as dialkyl sulfate, or aryl sulfonate ester, a hydrocarbyl iodide, or a material having an active halide such as allyl chloride or bromide, etc.

The alkylphenols which are suitable for use as precursors for the compounds of this invention are prepared by conventional techniques employing as alkylating agents monoolefins, alcohols, alkyl halides, etc. The reaction may be effected by thermal methods or with a catalyst. The alkylphenols prepared by thermal alkylation with a linear alpha olefin have a high proportion of aryl attachment on the 1 or 2 carbon of the alkyl chain, (i.e., end group attachment), and when sulfonated and capped produce a particularly effective detergent. The preferred materials will have at least 90% end group attachment. The catalysts which may be employed include conventional Friedel-Crafts catalysts such as aluminum chloride, zinc chloride, etc; activated clay; and various other materials such as metal phenoxides, particularly those of aluminum and magnesium; hydrogen fluoride treated aluminum silicates; alkyl sulfonic acids; benzene sulfonic acid; naphthalene sulfonic acid; transitional alumina; and calcium and indium oxides, etc.

The sulfonation of the alkylphenols to produce compounds of the invention may be accomplished by any suitable method. Thus, materials which may be effectively reacted with the alkylphenols include chlorosulfonic acid, oleum, or sulfuric acid. Sulfonation with oleum is preferred.

The sulfonation is usually accomplished with a ratio of at least 2 and preferably from 4 to 10 mols of available $SO_3$ from the sulfonating agent to one mol of the alkylphenol. The use of a solvent is ordinarily not required in carrying out the sulfonation. The alkylphenol and the sulfonating agent are simply mixed, and the reaction is allowed to proceed, maintaining the temperature of the reaction mixture within desired limits. The time required for disulfonation will be dependent upon the reaction temperature, the sulfonating agent, the ratio of sulfonating agent to alkylphenol, and the total quantity of reactants present. The reaction is usually effected at a temperature in the range of 0° to 150° C., preferably 25° to 100° C. The product will usually contain at least 75% of material containing two sulfonate groups per molecule with the balance containing one sulfonate group per molecule.

The production of the compounds of this invention is effected by replacing the phenolic hydrogen with a hydrocarbyl group as previously defined. This is effected by neutralizing the disulfonic acid alkylphenol with a water-soluble salt-forming cationic neutralizing agent, usually a metal oxide or hydroxide, and preferably an alkaline earth metal or alkali metal hydroxide. The alkali metal hydroxides are preferred, and most preferred is sodium hydroxide. Sufficient quantity of the neutralizing agent is added to convert the phenolic hydroxyl group to a phenoxide of the selected cation. This is accomplished by employing at least three mols of the neutralizing agent to one mol of the disulfonic acid.

The hydrocarbyl capping is effected by reacting the phenoxide with an agent such as a dialkyl sulfate including dimethyl sulfate, diethyl sulfate, dipropyl sulfate, etc., an iodide such as methyl iodide, ethyl iodide, etc., an unsaturated aliphatic compound containing active halide such as allylchloride or methylallylchloride, or an aralkyl material also containing an active halogen such as benzyl chloride or isomers of tolylmethyl chloride. The substitution reaction is accomplished by contacting the phenoxide with at least one and preferably from about 1.1 to 3 mols of the agent for each mol of phenoxide.

After the hydrocarbyl capping reaction the material may be blended with conventional detergent additives to formulate liquid heavy duty detergents. Alternatively, water in the product may be removed in any quantity to complete dryness by conventional concentration techniques such as evaporation, distillation, drum drying, etc., to yield a concentrated solution, a slurry, or a dry particulate solid which may then be blended to form a heavy duty detergent.

The solid product isolated as described above may be desalted by the usual procedures as used in the alkylbenzene sulfonate art. In this method the solid material is mixed with about a 70/30 alcohol/water solution. The insoluble inorganic sulfate is removed by filtration, and the organic surfactant may be used as such or isolated by evaporation of the solvent. The liquid concentrates and slurries may be treated in similar fashion with allowance made for the quantity of water already present. These desalting procedures give a detergent product that is essentially free of inorganic salt.

The following examples describe the preparation of the compounds of this invention.

EXAMPLE 1

In a round-bottom flask there was charged 11.20 g. (0.0025 mol) of a 12.87% solution of disodium $C_{18-20}$ alkylphenol disulfonate (the alkylphenol portion of which was produced by thermal alkylation of phenol with a $C_{18-20}$ alpha olefin mixture), 0.40 g. (0.005 mol) of a 50% solution of NaOH, and 0.63 g. (0.005 mol) of dimethyl sulfate. The resulting two-phase mixture was stirred at about 22° C. for four hours. At the end of 15 minutes the mixture had become homogenous. At the end of the four hours an ultraviolet absorption spectrum was taken in 0.01 N NaOH and no absorption was found at 308 m$\mu$ indicating that the phenolic hydroxyl groups had disappeared and that the product was alkylbenzene methoxy disulfonate.

EXAMPLE 2

The general procedure of Example 1 was followed except that only 0.0025 mol of sodium hydroxide was employed and the reaction time was two hours. The results were the same.

EXAMPLE 3

The procedure of Example 2 was followed except that only 0.0025 mol of dimethyl sulfate was employed. In this case only 55% of the hydroxyl groups were converted.

EXAMPLE 4

The procedure of Example 2 was followed except that 0.0055 mol of dimethyl sulfate was employed. Analysis indicated that all of the phenolic hydroxyl had been converted to methoxyl.

EXAMPLE 5

A mixture of 6.82 g. of a 22.7% solution of disodium $C_{16}$ alkylphenol disulfonate (0.003 mol), 0.70 ml. of 6N NaOH (0.0042 mol), 1.5 ml. of water, and 0.70 g. (0.0045 mol) of diethyl sulfate was stirred at room temperature overnight. At the end of the reaction ultraviolet absorption analysis showed at least 98% capping of the phenolic group.

EXAMPLE 6

A mixture of 10.0 g. of a pre-neutralized (pH 12.8) solution of disodium $C_{18}$-$C_{20}$ alkylphenol disulfonate (0.003 mol) and 0.56 g. of allyl bromide (0.0046 mol) was stirred at about 40° C. for approximately 2 hours. At the end of the reaction, ultraviolet absorption analysis showed complete capping of the phenolic group.

EXAMPLE 7

A mixture of 10.0 g. of a pre-neutralized (pH 12.8) solution of disodium $C_{18}$-$C_{20}$ alkylphenol disulfonate (0.003 mol) and 0.77 g. of benzyl bromide (0.0045 mol) was stirred at room temperature for about an hour. The mixture was still heterogeneous. It was heated up to 75° C and stirred at about 75° C. for four hours. At the end of the reaction ultraviolet absorption analysis showed at least 97% benzylation of the phenolic group.

EXAMPLE 8

The procedure of Example 7 was followed except that benzyl chloride was used instead of the bromide. A 90% benzylation was achieved.

EXAMPLE 9

Following the same procedure as Example 5 except that a disodium $C_{18}$ alkylphenol disulfonate having a high percent of ortho end group attachment was used. At the end of the reaction, on standing, a crystalline precipitate formed. It was isolated by filtration and dried.

The compounds of this invention are useful as heavy duty detergent actives. In the past, heavy duty detergent formulations useful for removing soil from textiles have comprised an organic surfactant (detergent) and an inorganic phosphate builder; the phosphate being present by weight, in an amount of from one to four times that of the detergent. The compounds of the present invention are excellent soil removers without the aid of any phosphate builder. That is, the compounds of this invention satisfy all need for both organic surfactant and builder in the final heavy duty detergent formulation. One way that this may be accomplished is by preparing a mixture of the disulfonate materials of the instant invention and an inert material, e.g. water, sodium sulfate, sodium carbonate, etc. Such mixtures may contain any amount of disulfonate in excess of about 10%, preferably 15% or more. One useful composition comprises from 30 to 50% disulfonate and the remainder, sodium sulfate. Many other combinations make useful formulations and may be either liquid solutions or particulate solids.

As heavy duty detergents, it is contemplated that the disulfonate compounds will be used in wash water at concentrations of about 0.01% to about 0.10%. This is within the same range of concentrations as are employed with the prent day commercial detergents. In other words, the soil removal properties of the present compounds are essentially equivalent to the soil removal properties of an equal amount of the current commercial surfactant combined with at least an equal amount of phosphate.

Detergency of the compounds of the present invention is measured by their ability to remove natural sebum soil from cotton cloth. By this method, small swatches of cloth, soiled by rubbing over face and neck, are washed with test solutions of detergents in a miniature laboratory washer. The quantity of soil removed by this washing procedure is determined by measuring the reflectances of the new cloth, the soiled cloth, and the washed cloth, and other unknown variables, the absolute value of percent soil removal is not an accurate measure of detergent effectiveness and cannot be used to compare various detergents. Therefore, the art has developed the method of using relative detergency ratings for comparing detergent effectiveness.

The relative detergency ratings are obtained by comparing and correlating the percent soil removal results from solutions containing the detergents being tested with the results from two defined standard solutions. The two standard solutions are selected to represent a detergent system exhibiting relatively high detersive characteristics and a system exhibiting relatively low detersive characteristics. The systems are assigned detergency ratings of 6.3 and 2.2 respectively.

By washing portions of each soiled cloth with the standardized solutions, as well as with two test solutions, the results can be accurately correlated. The two standard solutions are identical in formulation but are employed at different hardnesses.

| Standard Solution Formulation | |
|---|---|
| Ingredient | Weight % |
| Linear Alkylbenzene sulfonate (LAS) | 25 |
| Sodium triphosphate | 40 |
| Water | 8 |
| Sodium sulfate | 19 |
| Sodium silicate | 7 |
| Carboxymethylcellulose | 1 |

The standard exhibiting high detersive characteristics (Control B) is prepared by dissolving the above formulation (1.0 g.) in one liter of 50 ppm hard water (calculated as ⅔ calcium carbonate and ⅓ magnesium carbonate). The low detersive standard (Control A) contained the formulation (1.0 g.) dissolved in one liter of 180 ppm water (same basis).

A miniature laboratory washer is so constructed that four different solutions can be used to wash different parts of the same swatch. This arrangement ensures that all four solutions are working on identical soil (natural facial soil). Relative detergency ratings (RDRs) are calculated from soil removals (SRs) according to the equation:

$$RDR = 2.2 + 4.1 \frac{\% SR_{Test} - \% SR_{Control\ A}}{\% SR_{Control\ B} - \% SR_{Control\ A}}$$

A further refinement in the determination of relative detergency ratings was developed. In this method, instead of employing two standard formulations, one of the formulations used in preparing the four test solutions had a known relative detergency rating (RDR) which had been determined by the above formula. Relative detergency ratings of the other three formulations were then determined by comparing the percent soil removal (SR) of these formulations with that of the known formulation.

In the series of tests, each test result represents the average of at least four replicate determinations in the laboratory washer. In setting up the washer each sample was placed in individual barrels of the washer in a random manner.

The following table presents the detergency data on a group of representative hydrocarbyloxylbenzene disulfonates. For comparison, the detergency rating is given for a linear alkylbenzene sulfonate (LAS) (having from 11 to 14 carbon atom straight chain alkyl groups) both with and without a phosphate builder.

Each formulation of the instant invention tested comprised 25 weight percent of the test material along with 1% carboxymethylcellulose, 7% sodium silicate, 8% water, and 59% sodium sulfate. The LAS comparison formulation without phosphate was prepared in the same way. The LAS-phosphate formulation contained 20% LAS, 40% sodium triphosphate, 1% carboxymethyl-cellulose, 7% sodium silicate, 8% water and 24% sodium sulfate. The test results were obtained at a pH of 7 except for the two LAS examples, which were run at a pH of 9 (without phosphate) and 10 (with phosphate). The tests were run at concentrations of 0.1 and 0.15% by weight in water. The alkylphenols were those produced by catalytic and thermal alkylation with alpha olefins and internal olefins. Those produced by thermal alkylation with an alpha olefin and thus having high end group attachment are indicated by an asterisk.

| | | | Relative Detergency Ratings | | |
|---|---|---|---|---|---|
| | | | 50 ppm H$_2$O | | 180 ppm H$_2$O |
| Type | Hydrocarbyl Group (Y) | Alkyl Group (R) Number Carbon Atoms | 0.10 % Conc. | 0.15 % Conc. | 0.15% Conc. |
| Linear Alkylbenzene Sulfonate (LAS) (25%) (11 – 14 carbon atom alkyl group) | — | — | 2.8 | 3.8 | 0.5 |
| Linear Alkylbenzene Sulfonate (20%) and Trisodium Phosphate (40%) | — | — | 5.8 | 6.2 | 3.7 |
| Linear Alkyl Hydrocarbyloxybenzene Disulfonate | Methyl | 14 | 3.5* | | 3.1* |
| Linear Alkyl Hydrocarbyloxybenzene Disulfonate | " | 16 | 5.2* | | 3.7* |
| Linear Alkyl Hydrocarbyloxybenzene Disulfonate | " | " | | 3.2 | 2.4 |
| Linear Alkyl Hydrocarbyloxybenzene Disulfonate | " | 18 | | 5.3 | 4.5 |
| Linear Alkyl Hydrocarbyloxybenzene Disulfonate | " | " | 5.3* | | 3.6* |
| Linear Alkyl Hydrocarbyloxybenzene Disulfonate | " | 18 – 20 Mixture | | 5.1 | 3.6 |
| Linear Alkyl Hydrocarbyloxybenzene Disulfonate | " | 20 | | 4.9 | 4.0 |
| Linear Alkyl Hydrocarbyloxybenzene Disulfonate | " | 21 | | 4.7 | 4.0 |
| Linear Alkyl Hydrocarbyloxybenzene Disulfonate | " | 22 | | 4.0 | 3.5 |
| Linear Alkyl Hydrocarbyloxybenzene Disulfonate | " | 15 – 20 Mixture | 5.0* | | 3.8* |
| Linear Alkyl Hydrocarbyloxybenzene Disulfonate | Allyl | 14 | 2.6 | | 2.3 |
| Linear Alkyl Hydrocarbyloxybenzene Disulfonate | " | 16 | 4.2 | | 2.8 |
| Linear Alkyl Hydrocarbyloxybenzene Disulfonate | " | 18 – 20 Mixture | 4.7 | | 2.9 |
| Linear Alkyl Hydrocarbyloxybenzene Disulfonate | Benzyl | 14 | 3.5 | | 2.4 |
| Linear Alkyl Hydrocarbyloxybenzene Disulfonate | " | 18 – 20 Mixture | 4.8 | | 2.9 |

In another detergency test procedure the detergent effectiveness of the ethyloxy derivative was found to be equivalent to the corresponding methoxy compound.

These data show clearly the effectiveness of the hydrocarbyloxybenzene disulfonates in nonphosphate detergent activity. It may be noted that the methoxy materials, particularly those having from 16 to 18 carbon atoms and a high percentage of end group attachment are very close in detergency to LAS/phosphate combination and achieve this effectiveness without any builder.

The detergent compounds of this invention are of light color, are stable in storage, and in aqueous solutions are stable in the presence of both hypochlorite and oxygen-containing bleaches.

The hydrocarbyl capped alkylphenol disulfonates may be employed in combination with other detergent active materials. They are particularly effective with other dianionic materials, examples of which include linear alkyl and alkenyl disulfates and disulfonates. A particularly useful class of materials for use in detergent active combinations is that of linear 2-alkenyl or linear 2-alkyl 1,4-butane diol disulfates in which the alkenyl or alkyl groups contain from 15 to 20 carbon atoms. Another useful class is the alkylphenol disulfonates which may be present in from 0.1 to 20% by weight.

In employing the detergent active materials of this invention in detergent compositions, they may be formulated with additional compatible ingredients being optionally incorporated to enhance the detergent properties. Such materials may include but are not limited to anticorrosion, antiredeposition, bleaching and sequestering agents, and certain organic and inorganic alkali metal and alkaline earth metal salts such as inorganic sulfates, carbonates, or borates. Also nonphosphate builders may be included in the composition. Examples of these builders are the sodium salts of nitrilotriacetic acid, ethylene diamine tetraacetic acid, and ethylene maleic acid copolymers, etc. Also small quantities of phosphate builders may be included although, of course, they are not necessary for effective detergency.

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

I claim:

1. Detergent active materials capable of heavy duty washing in the absence of phosphates consisting of linear alkyl hydrocarbyloxybenzene disulfonates of the formula

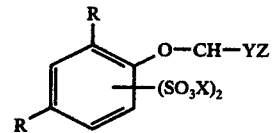

in which one R is linear alkyl of 16 to 21 carbon atoms and the other is H, X is H or an alkali metal, Y and Z are H.

2. The detergent active material of claim 1, in which at least 90% of the alkyl groups represented by R are attached through the 1 or 2 carbon atom of the alkyl group.

* * * * *